United States Patent
Zergiebel et al.

(10) Patent No.: US 9,949,737 B2
(45) Date of Patent: Apr. 24, 2018

(54) ADAPTER ASSEMBLIES FOR INTERCONNECTING SURGICAL LOADING UNITS AND HANDLE ASSEMBLIES

(71) Applicant: Covidien LP, Mansfield, MA (US)

(72) Inventors: Earl Zergiebel, Guilford, CT (US); David Chowaniec, Rocky Hill, CT (US); Ryan Williams, New Hartford, CT (US); Anand Subramanian, Stamford, CT (US)

(73) Assignee: Covidien LP, Mansfield, MA (US)

( * ) Notice: Subject to any disclaimer, the term of this patent is extended or adjusted under 35 U.S.C. 154(b) by 447 days.

(21) Appl. No.: 14/811,328

(22) Filed: Jul. 28, 2015

(65) Prior Publication Data
US 2016/0113648 A1    Apr. 28, 2016

Related U.S. Application Data

(60) Provisional application No. 62/066,983, filed on Oct. 22, 2014.

(51) Int. Cl.
*A61B 17/072*    (2006.01)
*H01H 9/06*    (2006.01)
(Continued)

(52) U.S. Cl.
CPC ...... *A61B 17/072* (2013.01); *A61B 17/07207* (2013.01); *F16C 1/12* (2013.01);
(Continued)

(58) Field of Classification Search
CPC .. H01H 9/06; A61B 17/072; A61B 17/07207; A61B 2090/0803; A61B 2090/0808;
(Continued)

(56) References Cited

U.S. PATENT DOCUMENTS 2,777,340 A    1/1957    Hettwer et al.
2,957,353 A    10/1960    Babacz
(Continued)

FOREIGN PATENT DOCUMENTS

AU    2008229795 A1    4/2009
CA    2451558 A1    1/2003
(Continued)

OTHER PUBLICATIONS

European Search Report dated Apr. 1, 2016, corresponding to European Application No. 15190760.7; 7 pages.
(Continued)

*Primary Examiner* — Michelle Lopez

(57) ABSTRACT

A surgical instrument includes a handle assembly, a surgical loading unit, and an adapter assembly coupled therebetween. The adapter assembly includes a housing, an elongated body, a switch assembly, and a switch actuator. The elongated body extends distally from the housing and is configured to be coupled to the surgical loading unit. The switch assembly is disposed within the housing and configured to communicate that the surgical loading unit is coupled to the elongated body. The switch assembly includes a substrate, a switch mounted on the substrate, and at least one wire coupled to the substrate. The switch actuator is movably disposed within the housing and configured to actuate the switch upon engagement of the surgical loading unit with the elongated body.

21 Claims, 4 Drawing Sheets

(51) Int. Cl.

| | | |
|---|---|---|
| *A61B 90/90* | (2016.01) | |
| *H01H 15/10* | (2006.01) | |
| *F16C 1/12* | (2006.01) | |
| *H01H 13/81* | (2006.01) | |
| *A61B 17/00* | (2006.01) | |
| *A61B 19/00* | (2006.01) | |
| *A61B 90/00* | (2016.01) | |

(52) U.S. Cl.
CPC ............ *H01H 9/06* (2013.01); *H01H 15/102* (2013.01); *A61B 90/90* (2016.02); *A61B 2017/00017* (2013.01); *A61B 2017/0046* (2013.01); *A61B 2017/00398* (2013.01); *A61B 2017/00473* (2013.01); *A61B 2017/00477* (2013.01); *A61B 2017/07271* (2013.01); *A61B 2017/07285* (2013.01); *A61B 2019/4857* (2013.01); *A61B 2090/0803* (2016.02); *A61B 2090/0808* (2016.02); *A61B 2090/0812* (2016.02); *H01H 13/81* (2013.01); *H01H 15/107* (2013.01); *H01H 2221/014* (2013.01); *H01H 2237/004* (2013.01); *H01H 2300/014* (2013.01); *H01H 2300/032* (2013.01)

(58) Field of Classification Search
CPC ............ A61B 2090/0812; A61B 90/90; A61B 2017/00017; A61B 2017/00398; A61B 2017/0046; A61B 2017/00473; A61B 2017/00477; A61B 2017/07271
USPC ....................................................... 227/180.1
See application file for complete search history.

(56) References Cited

U.S. PATENT DOCUMENTS

| | | | |
|---|---|---|---|
| 3,111,328 A | 11/1963 | Di Rito et al. | |
| 3,695,058 A | 10/1972 | Keith, Jr. | |
| 3,734,515 A | 5/1973 | Dudek | |
| 3,759,336 A | 9/1973 | Marcovitz et al. | |
| 4,162,399 A | 7/1979 | Hudson | |
| 4,606,343 A | 8/1986 | Conta et al. | |
| 4,705,038 A | 11/1987 | Sjostrom et al. | |
| 4,722,685 A | 2/1988 | de Estrada et al. | |
| 4,823,807 A | 4/1989 | Russell et al. | |
| 4,874,181 A | 10/1989 | Hsu | |
| 5,129,118 A | 7/1992 | Walmesley | |
| 5,129,570 A | 7/1992 | Schulze et al. | |
| 5,152,744 A | 10/1992 | Krause et al. | |
| RE34,556 E | 3/1994 | Sjostrom et al. | |
| 5,301,061 A | 4/1994 | Nakada et al. | |
| 5,312,023 A | 5/1994 | Green et al. | |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,411,508 A | 5/1995 | Bessler et al. | |
| 5,413,267 A | 5/1995 | Solyntjes et al. | |
| 5,427,087 A | 6/1995 | Ito et al. | |
| 5,467,911 A | 11/1995 | Tsuruta et al. | |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,540,706 A | 7/1996 | Aust et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,609,560 A | 3/1997 | Ichikawa et al. | |
| 5,632,432 A | 5/1997 | Schulze et al. | |
| 5,647,526 A | 7/1997 | Green et al. | |
| 5,653,374 A | 8/1997 | Young et al. | |
| 5,658,300 A | 8/1997 | Bito et al. | |
| 5,662,662 A | 9/1997 | Bishop et al. | |
| 5,667,517 A | 9/1997 | Hooven | |
| 5,693,042 A | 12/1997 | Boiarski et al. | |
| 5,704,534 A | 1/1998 | Huitema et al. | |
| 5,713,505 A | 2/1998 | Huitema | |
| 5,762,603 A | 6/1998 | Thompson | |
| 5,779,130 A | 7/1998 | Alesi et al. | |
| 5,782,396 A | 7/1998 | Mastri et al. | |
| 5,782,397 A | 7/1998 | Koukline | |
| 5,797,536 A | 8/1998 | Smith et al. | |
| 5,820,009 A | 10/1998 | Melling et al. | |
| 5,863,159 A | 1/1999 | Lasko | |
| 5,908,427 A | 6/1999 | McKean et al. | |
| 5,954,259 A | 9/1999 | Viola et al. | |
| 5,964,774 A | 10/1999 | McKean et al. | |
| 5,993,454 A | 11/1999 | Longo | |
| 6,010,054 A | 1/2000 | Johnson et al. | |
| 6,017,354 A | 1/2000 | Culp et al. | |
| 6,032,849 A | 3/2000 | Mastri et al. | |
| 6,045,560 A | 4/2000 | McKean et al. | |
| 6,090,122 A | 7/2000 | Sjostrom et al. | |
| 6,090,123 A | 7/2000 | Culp et al. | |
| 6,126,651 A | 10/2000 | Mayer | |
| 6,129,547 A | 10/2000 | Cise et al. | |
| 6,165,169 A | 12/2000 | Panescu et al. | |
| 6,239,732 B1 | 5/2001 | Cusey | |
| 6,241,139 B1 | 6/2001 | Milliman et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,371,909 B1 | 4/2002 | Hoeg et al. | |
| 6,434,507 B1 | 8/2002 | Clayton et al. | |
| 6,443,973 B1 | 9/2002 | Whitman | |
| 6,461,372 B1 | 10/2002 | Jensen et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,645,218 B1 | 11/2003 | Cassidy et al. | |
| 6,654,999 B2 | 12/2003 | Stoddard et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,743,240 B2 | 6/2004 | Smith et al. | |
| 6,783,533 B2 | 8/2004 | Green et al. | |
| 6,792,390 B1 | 9/2004 | Burnside et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,899,538 B2 | 5/2005 | Matoba | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 6,986,451 B1 | 1/2006 | Mastri et al. | |
| 6,988,649 B2 | 1/2006 | Shelton, IV et al. | |
| 7,032,798 B2 | 4/2006 | Whitman et al. | |
| RE39,152 E | 6/2006 | Aust et al. | |

(56) References Cited

U.S. PATENT DOCUMENTS

| | | |
|---|---|---|
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,887,559 B2 | 2/2011 | Deng et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2007/0023476 A1 | 2/2007 | Whitman et al. |
| 2007/0023477 A1 | 2/2007 | Whitman et al. |

(56) References Cited

U.S. PATENT DOCUMENTS

| | | |
|---|---|---|
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0023022 A1 | 1/2010 | Zeiner et al. |
| 2010/0069942 A1 | 3/2010 | Shelton, IV |
| 2010/0193568 A1 | 8/2010 | Scheib |
| 2010/0211053 A1 | 8/2010 | Ross et al. |
| 2010/0225073 A1 | 9/2010 | Porter et al. |
| 2010/0320252 A1 | 12/2010 | Viola et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2263568 A2 | 12/2010 |
| EP | 2272443 A1 | 1/2011 |

(56) References Cited

FOREIGN PATENT DOCUMENTS

| | | | |
|---|---|---|---|
| EP | 2316345 | A1 | 5/2011 |
| EP | 2324776 | A2 | 5/2011 |
| EP | 2329773 | A1 | 6/2011 |
| EP | 2333509 | A1 | 6/2011 |
| EP | 2462878 | A1 | 6/2012 |
| EP | 2462880 | A2 | 6/2012 |
| EP | 2491872 | A1 | 8/2012 |
| EP | 2586382 | A2 | 5/2013 |
| EP | 2606834 | A2 | 6/2013 |
| EP | 2668910 | A2 | 12/2013 |
| EP | 2668912 | A2 | 12/2013 |
| EP | 2676615 | A2 | 12/2013 |
| ES | 2333509 | A1 | 2/2010 |
| JP | 08-038488 | | 2/1996 |
| JP | 2005-125075 | A | 5/2005 |
| KR | 20120022521 | A | 3/2012 |
| WO | 99/15086 | A1 | 4/1999 |
| WO | 2000/072760 | A1 | 12/2000 |
| WO | 2000/072765 | A1 | 12/2000 |
| WO | 2003/000138 | A2 | 1/2003 |
| WO | 2003/026511 | A1 | 4/2003 |
| WO | 2003/030743 | A2 | 4/2003 |
| WO | 2003065916 | A1 | 8/2003 |
| WO | 2003/077769 | A1 | 9/2003 |
| WO | 2003/090630 | A2 | 11/2003 |
| WO | 20041107989 | A1 | 12/2004 |
| WO | 20061042210 | A2 | 4/2006 |
| WO | 2007016290 | A2 | 2/2007 |
| WO | 20071026354 | A1 | 3/2007 |
| WO | 2007137304 | A2 | 11/2007 |
| WO | 2008/131362 | A2 | 10/2008 |
| WO | 2008/133956 | A2 | 11/2008 |
| WO | 2009/039506 | A1 | 3/2009 |
| WO | 2007014355 | A3 | 4/2009 |
| WO | 2009/132359 | A2 | 10/2009 |
| WO | 2009/143092 | A1 | 11/2009 |
| WO | 2009/149234 | A1 | 12/2009 |
| WO | 2011014314 | A1 | 2/2011 |
| WO | 2011/108840 | A2 | 9/2011 |
| WO | 2012040984 | A1 | 4/2012 |

OTHER PUBLICATIONS

Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
European Communication dated May 11, 2017, corresponding to European Application No. 15190760.7; 3 pages.

ADAPTER ASSEMBLIES FOR INTERCONNECTING SURGICAL LOADING UNITS AND HANDLE ASSEMBLIES

BACKGROUND

This application claims the benefit of and priority to U.S. Provisional Patent Application No. 62/066,983 filed Oct. 22, 2014, the entire disclosure of which is incorporated by reference herein.

BACKGROUND

1. Technical Field

The present disclosure relates to adapter assemblies for use with an electromechanical surgical system and their methods of use. More specifically, the present disclosure relates to hand-held, electromechanical surgical instruments capable of detecting a presence of a loading unit and/or identifying one or more parameters of a loading unit attached to an adapter assembly.

2. Background of Related Art

Linear clamping, cutting, and stapling surgical devices may be employed in surgical procedures to resect tissue. Conventional linear clamping, cutting, and stapling devices include a handle assembly, an elongated shaft and a distally located surgical loading unit. The loading unit includes a pair of gripping members, which clamp about tissue to be stapled. One of the gripping members includes a staple cartridge receiving region and a mechanism for driving the staples up through tissue and against an anvil portion on the other gripping member.

In many instances, the handle assembly is reusable and the loading unit is disposable. The disposable loading unit may be selectively coupled to the handle assembly via an adapter assembly prior to use and then disconnected from the adapter assembly and therefore decoupled from the reusable handle assembly following use in order to be disposed of or in some instances sterilized for re-use.

A need exists for various types of adapter assemblies that communicate relevant information to a handle assembly of a surgical instrument upon a proper engagement of a loading unit with the handle assembly.

SUMMARY

The present disclosure relates to adapter assemblies for use between handle assemblies and loading units. The present disclosure also relates to switch assemblies of an adapter assembly that effectively communicate information about a loading unit to a handle assembly, which is coupled to the adapter assembly, upon engagement of the loading unit with the handle assembly.

In an aspect of the present disclosure, an adapter assembly is provided. The adapter assembly includes a housing, an elongated body, a switch assembly and a switch actuator. The housing is configured to be coupled to a handle assembly. The elongated body defines a longitudinal axis along a length thereof and extends distally from the housing. The elongated body is configured to be coupled to a surgical loading unit. The switch assembly is disposed within the housing and configured to communicate that the surgical loading unit is coupled to the elongated body. The switch assembly includes a substrate, a switch, and at least one wire. The substrate has a top surface and a bottom surface. The switch is mounted on the top surface of the substrate. The wire is coupled to the substrate. The switch actuator is movably disposed within the housing and configured to actuate the switch upon engagement of the surgical loading unit with the elongated body.

In embodiments, the substrate may include a step disposed at an end thereof. The step may have a first planar surface that extends perpendicularly from the top surface of the substrate and a second planar surface extending perpendicularly from the first planar surface and being parallel with the top and bottom surfaces of the substrate. The wire may be coupled to the first planar surface and may extend along the longitudinal axis of the elongated body. The wire may include a first portion coupled to the second planar surface extending perpendicularly therefrom and a second portion extending perpendicularly from the first portion and along the longitudinal axis of the elongated body.

In embodiments, the wire may be coupled to the bottom surface of the substrate and may extend along the longitudinal axis of the elongated body.

In embodiments, the switch assembly may further include a shim disposed within the housing and may define a channel along at least a portion of a length thereof. The substrate may be disposed on the shim. The shim may further define an opening through a thickness thereof. The substrate may include an annular notch defined in an end thereof and a portion of the wire may be disposed within the annular notch.

In embodiments, the switch actuator may include a resilient member in communication with the switch. The adapter assembly may further include a release button in communication with the resilient member. The release button may move between a first position, in which the resilient member engages the switch, and a second position, in which the resilient member disengages the switch.

In another aspect of the present disclosure, a surgical instrument is provided. The surgical instrument includes a handle assembly, a surgical loading unit, and an adapter assembly. The surgical loading unit has a proximal end and a distal end including an end effector. The adapter assembly has a housing configured to be coupled to the handle assembly and an elongated body extending distally from the housing and configured to be coupled to the proximal end of the surgical loading unit. The adapter assembly includes a switch assembly disposed therein and configured to communicate that the loading unit is coupled to the elongated body. The switch assembly includes a substrate, a switch, and at least one wire. The substrate has a top surface and a bottom surface. The switch is mounted on the top surface of the substrate. The wire is coupled to the substrate. The switch actuator is movably disposed within the housing and configured to actuate the switch upon engagement of the surgical loading unit with the elongated body.

In embodiments, the substrate may include a plurality of layers. The plurality of layers may include a plurality of dielectric layers and at least one conductive layer disposed over at least one of the top surface, the bottom surface, or in between the plurality of dielectric layers. The substrate may include a plurality of vias interconnecting the switch and the at least one conductive layer.

In embodiments, the plurality of layers may define a first portion and a second portion. The first portion of the plurality of layers may include at least one dimension that is different than a corresponding dimension of the second portion of the plurality of layers to define a step. The step may include a first planar surface that extends perpendicularly from the first portion and a second planar surface extending perpendicularly from the first portion along the second portion.

In embodiments, the conductive layer may be disposed between the first portion and the second portion and may include at least one contact disposed on at least one of the first planar surface or the second planar surface of the step. The wire may be coupled to the contact. The contact may be coupled to the first planar surface such that the wire extends along the longitudinal axis of the elongated body. The contact may be coupled to the second planar surface. A first portion of the wire may extend perpendicularly from the second planar surface and a second portion of the wire may extend perpendicularly from the first portion of the wire and along the longitudinal axis of the elongated body.

BRIEF DESCRIPTION OF THE DRAWINGS

Embodiments of the present disclosure are described herein with reference to the accompanying drawings, wherein.

DETAILED DESCRIPTION

Figure 1A:
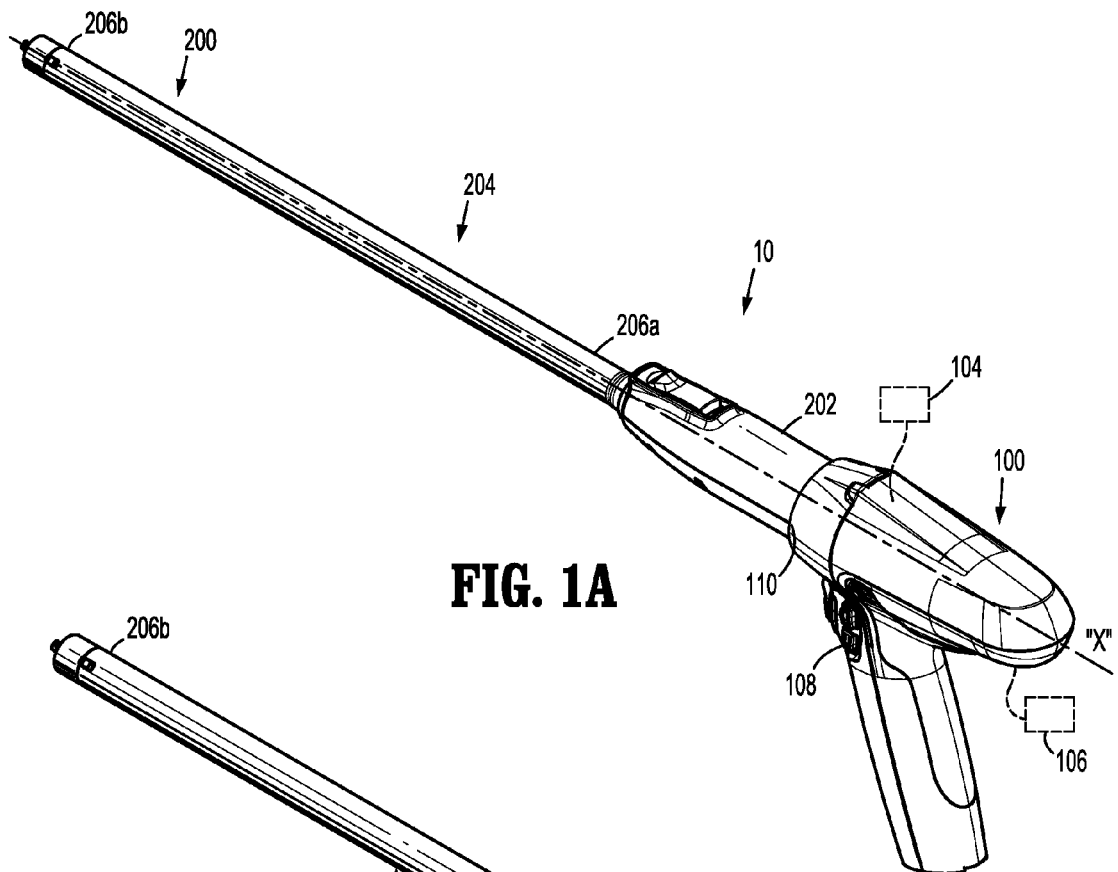
FIG. 1A is a perspective view of components of a hand-held, electromechanical surgical instrument, in accordance with an embodiment of the present disclosure.

Embodiments of the presently disclosed surgical instruments, surgical loading units, and adapter assemblies for electromechanical surgical devices and/or handle assemblies are described in detail with reference to the drawings, in which like reference numerals designate identical or corresponding elements in each of the several views. As used herein, the term "distal" refers to that portion of the surgical instrument, adapter assembly, handle assembly, loading unit, or components thereof, farther from the user, while the term "proximal" refers to that portion of the surgical instrument, adapter assembly, handle assembly, loading unit, or components thereof, closer to the user. As used herein, the term "toggle" is defined as a transition between a first condition, in which a switch is engaged, and a second condition, in which the switch is disengaged.

Figure 1B:
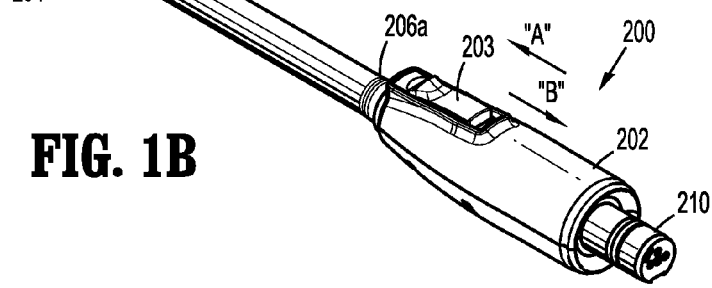
FIG. 1B is a perspective view of an adapter assembly of the surgical instrument shown in FIG. 1A.
Figure 1C:
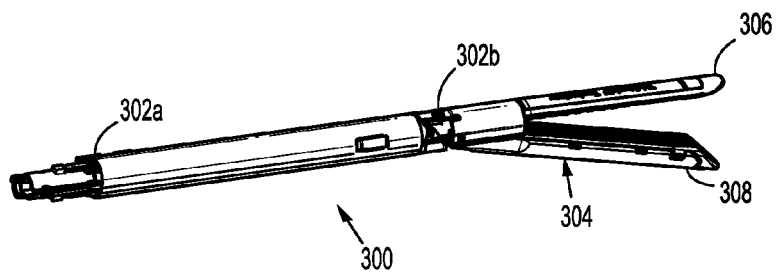
FIG. 1C is a side view of a surgical loading unit of the surgical instrument shown in FIG. 1A.

With reference to FIGS. 1A-1C, a surgical instrument, in accordance with an embodiment of the present disclosure, is generally designated as 10, and is in the form of a powered, hand-held, electromechanical surgical instrument 10. Surgical instrument 10 includes a handle assembly 100 configured for selective attachment thereto with any one of a number of adapter assemblies, such as, for example, adapter assembly 200, and, in turn, each unique adapter assembly 200 is configured for selective connection with any number of surgical loading units, such as, for example, loading unit 300. Loading unit 300 and adapter assembly 200 are configured for actuation and manipulation by handle assembly 100.

Reference may be made to International Publication No. WO 2009/039506 and U.S. Patent Application Publication No. 2011/0121049, the entire contents of both of which are incorporated herein by reference, for a detailed description of the construction and operation of an exemplary electromechanical, hand-held, powered surgical instrument.

Handle assembly 100 includes one or more controllers (not shown), a power source (not shown), a processor 104, and a drive mechanism having one or more motors 106, gear selector boxes (not shown), gearing mechanisms (not shown), and the like. Processor 104 is configured to control motors 106 and to detect a presence of a loading unit, for example, loading unit 300, and/or determine one or more parameters of loading unit 300, as described herein. Handle assembly 100 further includes a control assembly 108. Control assembly 108 may include one or more finger-actuated control buttons, rocker devices, joystick or other directional controls, whose input is transferred to the drive mechanism to actuate adapter assembly 200 and loading unit 300.

In particular, with reference to FIG. 1C, the drive mechanism is configured to drive shafts and/or gear components in order to selectively move an end effector 304 of loading unit 300 to rotate end effector 304 about a longitudinal axis "X" relative to handle assembly 100, to move an anvil assembly 306 relative to a cartridge assembly 308 of end effector 304, and/or to fire a stapling and cutting cartridge within cartridge assembly 308 of end effector 304.

With continued reference to FIG. 1A, handle assembly 100 defines a nose or connecting portion 110 configured to accept a corresponding drive coupling assembly 210 (FIG. 1B) of adapter assembly 200. Connecting portion 110 of handle assembly 100 has a cylindrical recess (not shown) that receives drive coupling assembly 210 of adapter assembly 200 when adapter assembly 200 is mated to handle assembly 100. Connecting portion 110 houses one or more rotatable drive connectors (not shown) that interface with corresponding rotatable connector sleeves (not shown) of adapter assembly 200.

When adapter assembly 200 is mated to handle assembly 100, each of the rotatable drive connectors of handle assembly 100 couples with a corresponding rotatable connector sleeve of adapter assembly 200. In this regard, the interface between the plurality of drive connectors of handle assembly 100 and the plurality of corresponding connector sleeves of the adapter assembly are keyed such that rotation of each of the drive connectors causes rotation of the corresponding connector sleeves of adapter assembly 200.

The mating of the drive connectors of handle assembly 100 with the connector sleeves of adapter assembly 200 allows rotational forces to be independently transmitted via each of the three respective connector interfaces. The drive connectors of handle assembly 100 are configured to be independently rotated by the drive mechanism.

Since each of the drive connectors of handle assembly 100 has a keyed and/or substantially non-rotatable interface with the respective connector sleeves of adapter assembly 200, when adapter assembly 200 is coupled to handle assembly 100, rotational force(s) are selectively transferred from drive mechanism of handle assembly 100 to adapter assembly 200.

With continued reference to FIGS. 1A-1C, the selective rotation of drive connector(s) of handle assembly 100 allows surgical instrument 10 to selectively actuate different functions of end effector 304. Selective and independent rotation of first drive connector of handle assembly 100 corresponds to the selective and independent opening and closing of end effector 304, and driving of a stapling/cutting component of end effector 304. Also, the selective and independent rotation of second drive connector of handle assembly 100 corresponds to the selective and independent articulation of end effector 304 about an articulation axis that is transverse to longitudinal axis "X." In particular, end effector 304 defines a second or respective longitudinal axis and is movable from a first position in which the second or respective longitudinal axis is substantially aligned with longitudinal axis "X" to at least a second position in which the second longitudinal axis is disposed at a non-zero angle with respect to longitudinal axis "X." Additionally, the selective and independent rotation of the third drive connector of handle assembly 100 corresponds to the selective and independent rotation of loading unit 300 about longitudinal axis "X" relative to handle assembly 100 of surgical instrument 10.

With continued reference to FIGS. 1A and 1B, adapter assembly 200 includes a housing, such as, for example, a knob housing 202 and an elongated body 204 extending from a distal end of knob housing 202. Elongated body 204 is dimensioned for endoscopic insertion. For example, elongated body 204 is passable through a typical trocar port, cannula or the like. Knob housing 202 is dimensioned to not enter the trocar port, cannula of the like. Elongated body 204 of adapter assembly 200 has a proximal portion 206a coupled to knob housing 202 and a distal portion 206b configured to be coupled to loading unit 300. Knob housing 202 is configured and dimensioned to house the components of adapter assembly 200 and to be coupled to handle assembly 100. Knob housing 202 includes a release button 203 in communication with a switch assembly 220 (see FIG. 3) of adapter assembly 200, as described in greater detail below.

Figure 2:
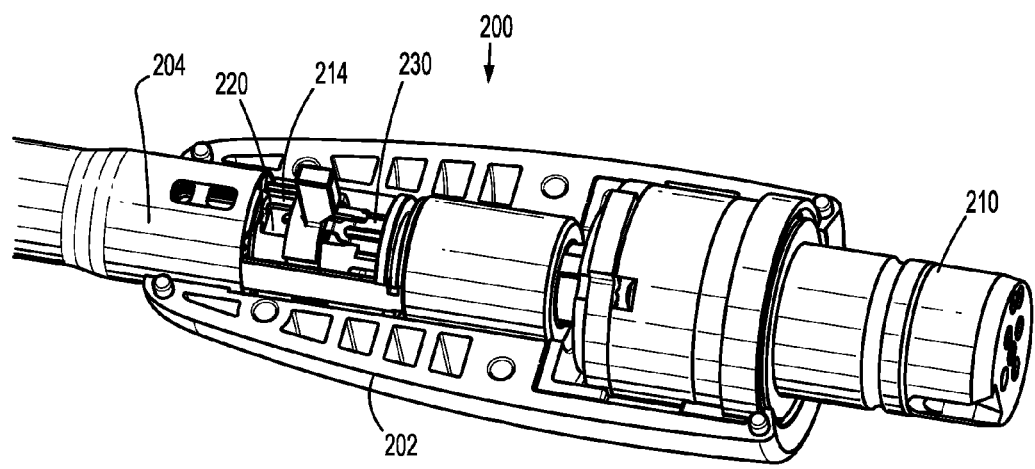
FIG. 2 is a cutaway view of a proximal portion of the adapter assembly shown in FIG. 1B.
Figure 3:
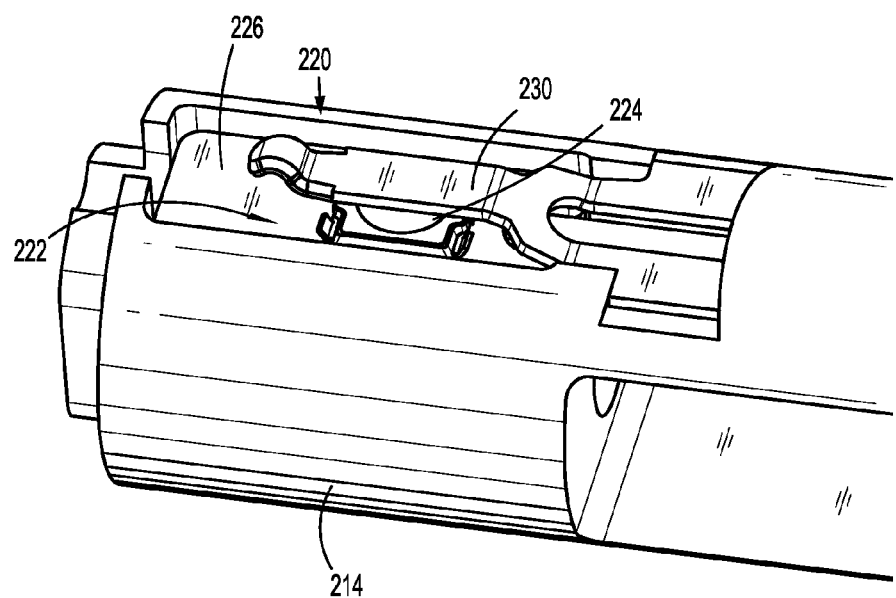
FIG. 3 is an enlarged view of a switch assembly and a switch actuator disposed within the proximal portion of the adapter assembly shown in FIG. 2.
Figure 4:
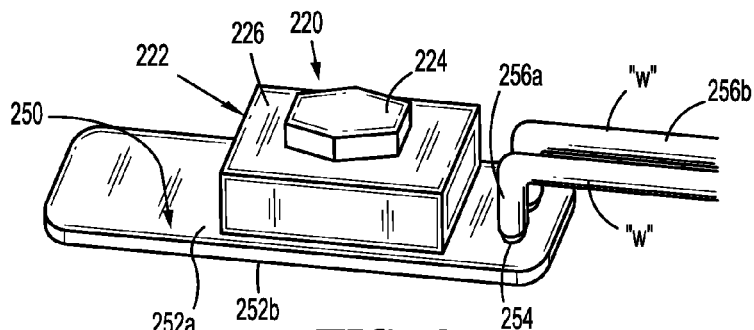
FIG. 4 is a perspective view of a switch assembly of the adapter assembly shown in FIG. 2.

With reference to FIGS. 2-4, knob housing 202 of adapter assembly 200 further includes a switch assembly 220 and a switch actuator, such as, for example, a leaf spring or resilient member 230 configured to actuate a switch 222 of switch assembly 220 in response to a coupling of loading unit 300 to distal portion 206b of elongated body 204. Switch assembly 220 includes switch 222, a substrate 250, and a pair of wires "W" (FIG. 4), connecting the switch 222 to processor 104. Switch assembly 220 is disposed within an inner housing 214, which is disposed within a distal end of knob housing 202. Switch 222 is mounted on substrate 230 and includes a button 224 and a platform 226. Button 224 is movable (e.g., resiliently depressible) relative to platform 226 in response to a downwardly oriented force being imparted thereon.

With specific reference to FIG. 3, resilient member 230 is movably disposed within inner housing 214. Resilient member 230 overlies or overlaps switch 222 and is configured to actuate switch 222 upon engagement of surgical loading unit 300 with distal end 206b of elongated body 204.

With specific reference to FIG. 4, substrate 250 mechanically supports switch 222 thereon and electrically connects switch 222 to processor 104 of handle assembly 100 via electrical wires "W," such that upon toggling of switch 222, switch 222 communicates to handle assembly 100 that loading unit 300 is lockingly engaged to distal portion 206b of elongated body 204 or that loading unit 300 is disengaged from distal portion 206b of elongated body 204. In embodiments, switch 222 may communicate with processor 104 using wireless communication, including various radio frequency protocols such as near field communication, radio frequency identification "RFID," BLUETOOTH®, (owned by Bluetooth SIG, Inc.), etc.

Substrate 250 may be in the form of a printed circuit board or an MMA board. Substrate 250 has a top surface 252a and a bottom surface 252b. Top surface 252a includes a pair of spaced apart electrical contacts 254. Wires "W" are coupled to respective electrical contacts 254 (e.g., via soldering). Wires "W" may be bent at any suitable angle, e.g., approximately at 90 degrees, to provide for connection between the wires "W" and contacts 254 and to define a first portion 256a and a second portion 256b of wires "W." First portion 256a of wire "W" is coupled to respective electrical contacts 254 and extends perpendicularly upward relative to top surface 252a of substrate 250. Second portion 256b of wire "W" extends perpendicularly from first portion 256a, such that second portion 256b of each electrical wire "W" is substantially parallel with respect to longitudinal axis "X."

With reference to FIG. 1C, as mentioned above, surgical instrument 10 includes loading unit 300. Loading unit 300 has a proximal portion 302a configured for engagement with distal end 206b of elongated body 204 of adapter assembly 200 and a distal portion 302b. Distal portion 302b of loading unit 300 has an end effector 304 extending therefrom. End effector 304 is pivotally attached to distal portion 302b. End effector 304 includes an anvil assembly 306 and a cartridge assembly 308. Cartridge assembly 308 is pivotable in relation to anvil assembly 306 and is movable between an open or unclamped position and a closed or clamped position for insertion through a cannula of a trocar.

Reference may be made to U.S. Pat. No. 7,819,896, entitled "TOOL ASSEMBLY FOR A SURGICAL STAPLING DEVICE", the entire content of which is incorporated herein by reference, for a detailed discussion of the construction and operation of a suitable end effector.

In operation, when proximal portion 302a of loading unit 300 is coupled to distal portion 206b of elongated body 204, release button 203 is moved in a distal direction, indicated by arrow "A" in FIG. 1B, from a second position or proximal position, in which switch 222 is disengaged, to a first position or distal position. As release button 203 moves from the proximal position to the distal position, release button 203 deflects resilient member 230 downwardly into engagement with switch 222 to toggle switch 222. When switch 222 is toggled, switch 222 communicates to handle assembly 100 that loading unit 300 is lockingly engaged to adapter assembly 200 and/or communicates to handle assembly 100 parameters pertaining to loading unit 300. The parameter may include a serial number of a loading unit, a type of a loading unit, a size of a loading unit, a staple size, information identifying whether the loading unit has been fired, a length of a loading unit, and/or a maximum number of uses of a loading unit.

To selectively release loading unit 300 from adapter assembly 200, release button 203 is moved or translated in a proximal direction, indicated by arrow "B" in FIG. 1B. As release button 203 moves from the distal position to the proximal position, release button 203 disengages resilient member 230 such that the resilient bias of resilient member 230 deflects resilient member 230 upwardly and out of engagement with switch 222. Upon resilient member 230 disengaging switch 222, switch 222 communicates to handle assembly 100 that loading unit 300 is no longer lockingly engaged with adapter assembly 200 and not ready for operation.

While an electrical interface between loading unit 300, adapter assembly 200, and/or handle assembly 100 is shown and described, it is contemplated that any other form or communication is within the scope of the present disclosure, for transmitting any or all of the operating parameters and/or the life-cycle information from loading unit 300 to handle assembly 100.

Figure 5:
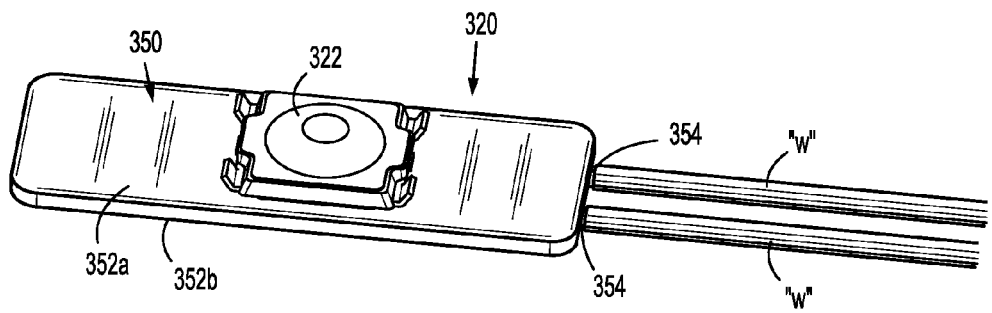
FIG. 5 is a perspective view of another embodiment of a switch assembly of the adapter assembly shown in FIG. 2.

With reference to FIG. 5, another embodiment of a switch assembly 320, which is substantially similar to switch assembly 220 discussed above, is provided. Contrasting with switch assembly 220, switch assembly 320 has a pair of wires "W" extending from a bottom surface 352b thereof. In particular, switch assembly 320 includes a switch 322, a substrate 350, and wires "W." Substrate 350 mechanically supports switch 322 thereon and electrically connects switch 322 with processor 104 of handle assembly 100 via electrical wires "W." Substrate 350 may be in the form of a printed circuit board or an MMA board. Substrate 350 has a top surface 352a and bottom surface 352b. Bottom surface 352b includes a pair of spaced apart electrical contacts 354. Wires "W" are coupled to respective electrical contacts 354 (e.g., via soldering). Accordingly, wires "W" extend from bottom surface 354 of substrate 350 and are substantially parallel to longitudinal axis "X" of elongated body 204.

Figure 6:
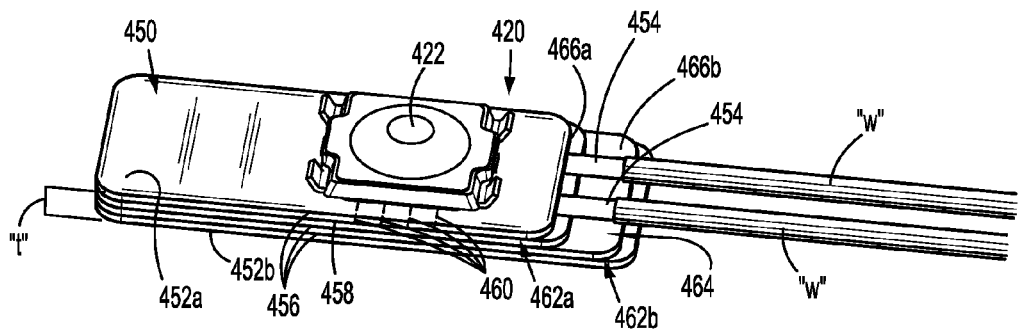
FIG. 6 is a perspective view of yet another embodiment of a switch assembly of the adapter assembly shown in FIG. 2.

With reference to FIG. 6, another embodiment of a switch assembly 420, which is substantially similar to switch assembly 220 discussed above, is provided. Switch assembly 420 also includes a switch 422, a substrate 450, and a pair of wires "W." Substrate 450 mechanically supports switch 422 thereon and electrically connects switch 422 with processor 104 of handle assembly 100 via electrical wires "W." Substrate 450 includes a top surface 452a and a bottom surface 452b and defines a thickness "t" of substrate 450 therebetween. Top and bottom surfaces 452a, 452b may be fabricated from a non-conductive material.

Substrate 450 includes a plurality of layers, such as, for example, a plurality of dielectric layers 456 disposed between top and bottom surfaces 452a, 452b and a conductive layer 458 disposed between dielectric layers 456. In some embodiments, one or more conductive layers may be disposed between dielectric layers or disposed on top surface 452a and/or bottom surface 452b of substrate 450. A plurality of vias 460 interconnect switch 422 and conductive layer 458. Layers 456, 458 define a first portion or top portion 462a of substrate 450 and a second portion or bottom portion 462b of substrate 450. Conductive layer 458 is disposed between top and bottom portions 462a, 462b.

First portion 462a of substrate 450 includes a dimension, such as, for example, a first length, that is different (e.g., less) than a corresponding dimension, such as, for example, a second length, of second portion 462b to define a step or cutout portion 464 disposed at an end of substrate 450. Step 464 has a first surface 466a having a planar configuration and a second surface 466b having a planar configuration. First surface 466a extends perpendicularly downward from top surface 452a of substrate 450 and defines a height, which may be about half of the thickness "t" of substrate 450. Second surface 466b extends perpendicularly from first surface 466a such that second surface 466b is substantially parallel with and disposed between top and bottom surfaces 452a, 452b of substrate 450. First surface 466a has a pair of spaced apart electrical contacts 454 attached thereto. Wires "W" are coupled to respective electrical contacts 454 (e.g., via soldering). Accordingly, wires "W" extend perpendicularly from first surface 466a of step 464 in line with longitudinal axis "X" of elongated body 204.

Figure 7:
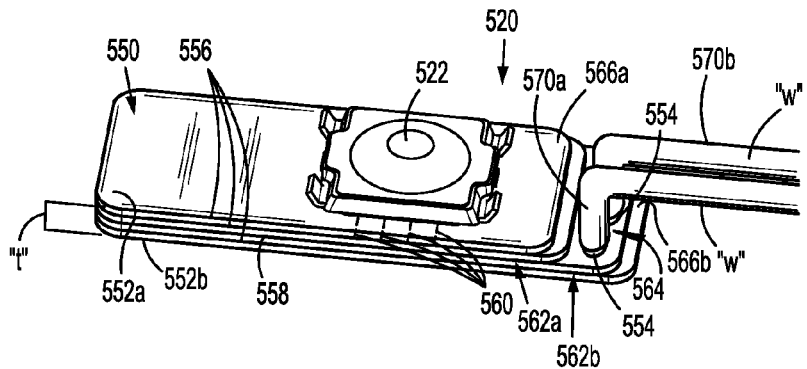
FIG. 7 is a perspective view of yet another embodiment of a switch assembly of the adapter assembly shown in FIG. 2.

With reference to FIG. 7, another embodiment of a switch assembly 520, which is substantially similar to switch assembly 420 discussed above, is provided. Contrasting with switch assembly 420, switch assembly 520 has a pair of bent wires "W" that extend perpendicularly upwardly from a second surface 566b of a step 564, as described herein. In particular, switch assembly 520 includes a switch 522, a substrate 550, and wires "W." Substrate 550 mechanically supports switch 522 thereon and electrically connects switch 522 with processor 104 of handle assembly 100 via electrical wires "W." Substrate 550 includes a top surface 552a and a bottom surface 552b and defines a thickness "t" of substrate 550 therebetween. Top and bottom surfaces 552a, 552b may be fabricated from a non-conductive material.

Substrate 550 includes a plurality of layers, such as, for example, a plurality of dielectric layers 556 disposed between top and bottom surfaces 552a, 552b and a conductive layer 558 disposed between dielectric layers 556. In some embodiments, one or more conductive layers may be disposed between dielectric layers or disposed on top surface 552a and/or bottom surface 552b of substrate 550. A plurality of vias 560 interconnect switch 522 and conductive layer 558. Layers 556, 558 define a first portion or top portion 562a of substrate 550 and a second portion or bottom portion 562b of substrate 550. Conductive layer 558 is disposed between top and bottom portions 562a, 562b of substrate 550.

First portion 562a of substrate 550 includes a dimension, such as, for example, a first length, that is different (e.g., less) than a corresponding dimension, such as, for example, a second length, of second portion 562b to define a step or cutout portion 564 disposed at an end of substrate 550. Step 564 has a first surface 566a having a planar configuration and a second surface 566b having a planar configuration. First surface 566a extends perpendicularly downward from top surface 552a of substrate 550 and defines a height, which may be about two-thirds of the thickness "t" of substrate 550. Second surface 566b extends perpendicularly from first surface 566a such that second surface 566b is substantially parallel with and disposed between top and bottom surfaces 552a, 552b of substrate 550. Second surface 566b has a pair of spaced apart electrical contacts 554 attached thereto.

Wires "W" are coupled to respective electrical contacts 554 (e.g., via soldering).

Wires "W" may be bent at any suitable angle, e.g., approximately at 90 degrees, to provide for connection between the wires "W" and contacts 554 and to define a first portion 570a and a second portion 570b of wires "W." First portion 570a of wires "W" extends perpendicularly upward from second surface 566b. Second portion 570b of wires "W" extends perpendicularly from first portion 570a of wires "W." Accordingly, second portion 570b of each wire "W" is substantially parallel with longitudinal axis "X."

Figure 8:
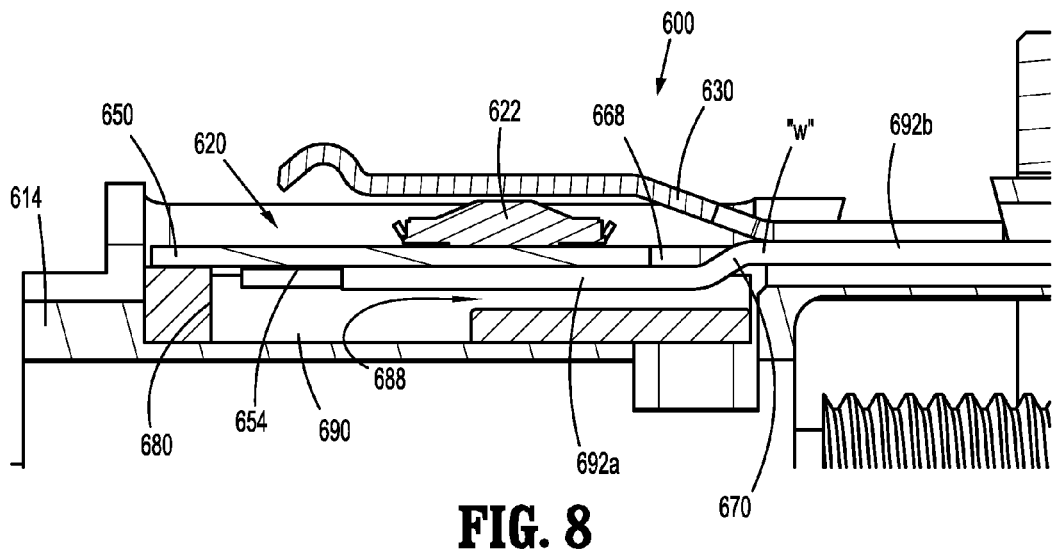
FIG. 8 is a cross sectional view of another embodiment of a proximal portion of an adapter assembly in accordance with the principles of the present disclosure.
Figure 9:
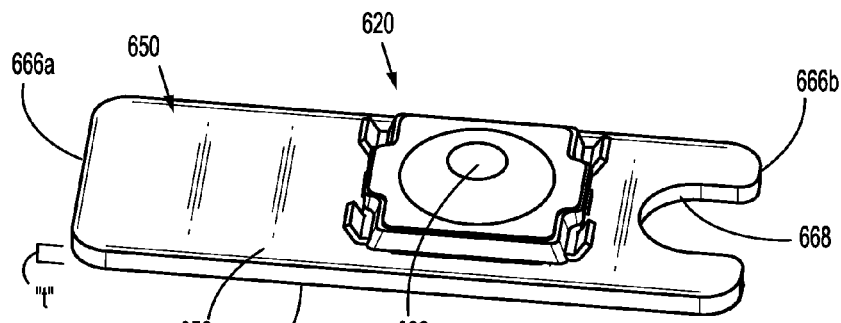
FIG. 9 is a perspective view of components of a switch assembly of the adapter assembly shown in FIG. 8.
Figure 10:
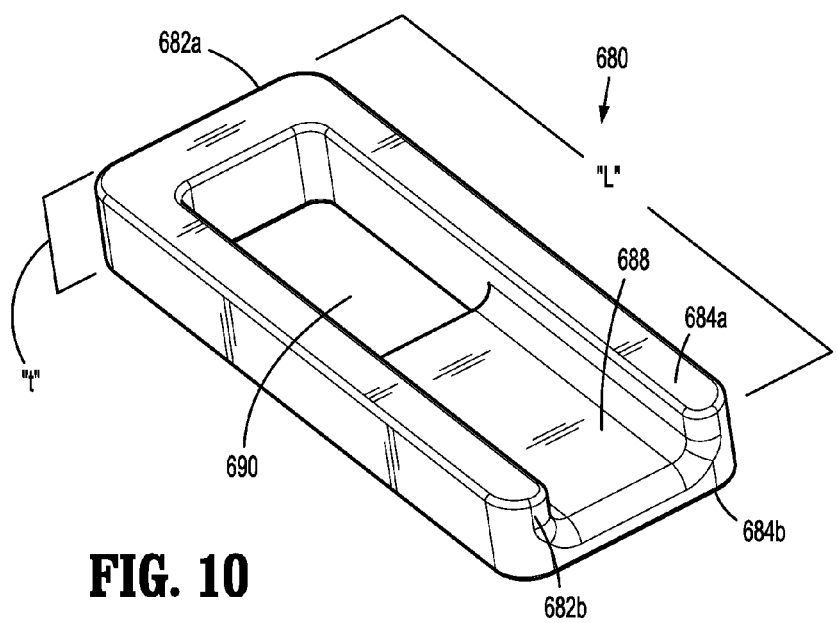
FIG. 10 is a perspective view of a shim of the switch assembly of the adapter assembly shown in FIG. 8.

With reference to FIGS. 8-10, another embodiment of an adapter assembly 600, which is similar to adapter assembly 200 discussed above, is provided. Adapter assembly 600 includes a switch assembly 620 and a switch actuator, such as, for example, a resilient member 630. Switch assembly 620 is disposed within an inner housing 614 of adapter assembly 600, which is disposed within knob housing 202 (see FIG. 1B). Resilient member 630 is configured to actuate a switch 622 of switch assembly 620 in response to a coupling of loading unit 300 (see FIG. 1C) to distal portion 206b of elongated body 204 (see FIG. 1B).

Switch assembly 620 includes switch 622, a substrate 650, a pair of electrical wires "W," and a shim 680. Substrate 650 mechanically supports switch 622 thereon and electrically connects switch 622 with processor 104 (see FIG. 1A) of handle assembly 100 via electrical wires "W." Substrate 650 may be in the form of a printed circuit board or an MMA board.

With reference to FIG. 9, substrate 650 has a top surface 652a and a bottom surface 652b and defines a thickness "t" of substrate 650 therebetween. Bottom surface 652b includes a pair of spaced apart electrical contacts 654 (see FIG. 8). Wires "W" are coupled to respective electrical contacts 654 (e.g., via soldering). Substrate 650 has a first end 666a and a second end 666b and defines a length of substrate 650 therebetween. Second end 666b includes an annular notch 668 defined therein configured for disposal of a bent portion 670 (see FIG. 8) of electrical wires "W," as described in greater detail below.

With specific reference to FIG. 10, shim 680 is disposed within inner housing 614 and supports substrate 650 thereon. Shim 680 has a rectangular configuration. In embodiments, shim 680 may be variously configured, such as, for example, oval, square, triangular, arcuate, polygonal, uniform, non-uniform, and/or tapered. Shim 680 includes a first end 682a and a second end 682b and defines a length "L" of shim 680 therebetween. Shim 680 includes a top surface 684a and a bottom surface 684b and defines a thickness "t" of shim 680 therebetween. Shim 680 defines a channel 688 along a portion of its length "L." Shim 680 further defines an opening or hole 690 that extends through the thickness "t" of shim 680 and is adjacent first end 682a of shim 680. Opening 690 is configured to provide access to bottom surface 652b of substrate 650 with a soldering tool to solder wires "W" to electrical contacts 654.

In assembly, with reference to FIG. 8, shim 680 is positioned within inner housing 614. Wires "W" are bent to form a first portion 692a and a second portion 692b. First portion 692a of wires "W" is disposed within channel 688 of shim 680 and in alignment with opening 690 of shim 680 such that second portion 692b is in line with longitudinal axis "X" of elongated body 204. Substrate 650 is positioned on top surface 684a of shim 680 such that bent portion 670 of each wire "W" is disposed within notch 668 defined in substrate 650. In this way, wires "W" are directed away from metal surfaces (e.g., resilient member 630) to prevent shorting.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

The invention claimed is:

1. An adapter assembly, comprising:
a housing configured to be coupled to a handle assembly;
an elongated body defining a longitudinal axis along a length thereof, the elongated body extending distally from the housing and being configured to be coupled to a surgical loading unit;
a switch assembly disposed within the housing and configured to communicate that the surgical loading unit is coupled to the elongated body, the switch assembly including:
a substrate having a top surface and a bottom surface;
a switch mounted on the top surface of the substrate; and
at least one wire coupled to the substrate; and
a switch actuator movably disposed within the housing and configured to actuate the switch upon engagement of the surgical loading unit with the elongated body.

2. The adapter assembly according to claim 1, wherein the substrate includes a step disposed at an end thereof, the step having a first planar surface that extends perpendicularly from the top surface of the substrate and a second planar surface extending perpendicularly from the first planar surface and being parallel with the top and bottom surfaces of the substrate.

3. The adapter assembly according to claim 2, wherein the at least one wire is coupled to the first planar surface and extends along the longitudinal axis of the elongated body.

4. The adapter assembly according to claim 2, wherein the at least one wire includes a first portion coupled to the second planar surface extending perpendicularly therefrom and a second portion extending perpendicularly from the first portion and along the longitudinal axis of the elongated body.

5. The adapter assembly according to claim 1, wherein the at least one wire is coupled to the bottom surface of the substrate and extends along the longitudinal axis of the elongated body.

6. The adapter assembly according to claim 1, wherein the switch assembly further includes a shim disposed within the housing and defining a channel along at least a portion of a length thereof, the substrate being disposed on the shim.

7. The adapter assembly according to claim 6, wherein the shim further defines an opening through a thickness thereof.

8. The adapter assembly according to claim 6, wherein the substrate includes an annular notch defined in an end thereof and a portion of the at least one wire is disposed within the annular notch.

9. The adapter assembly according to claim 1, wherein the switch actuator includes a resilient member in communication with the switch.

10. The adapter assembly according to claim 9, further comprising a release button in communication with the resilient member, wherein the release button moves between a first position, in which the resilient member engages the switch, and a second position, in which the resilient member disengages the switch.

11. A surgical instrument, comprising:
a handle assembly;
a surgical loading unit having a proximal end and a distal end including an end effector; and
an adapter assembly having a housing configured to be coupled to the handle assembly and an elongated body extending distally from the housing and configured to be coupled to the proximal end of the surgical loading unit, the adapter assembly including:
a switch assembly disposed therein and configured to communicate that the loading unit is coupled to the elongated body, the switch assembly including:
a substrate having a top surface and a bottom surface;
a switch mounted on the top surface of the substrate; and
at least one wire coupled to the substrate; and
a switch actuator movably disposed within the housing and configured to actuate the switch upon engagement of the surgical loading unit with the elongated body.

12. The surgical instrument according to claim 11, wherein the substrate includes a plurality of layers.

13. The surgical instrument according to claim 12, wherein the plurality of layers include a plurality of dielectric layers and at least one conductive layer disposed over at least one of the top surface, the bottom surface, or in between the plurality of dielectric layers.

14. The surgical instrument according to claim 13, wherein the substrate includes a plurality of vias interconnecting the switch and the at least one conductive layer.

15. The surgical instrument according to claim 13, wherein the plurality of layers defines a first portion and a second portion.

16. The surgical instrument according to claim 15, wherein the first portion of the plurality of layers includes at least one dimension that is different than a corresponding dimension of the second portion of the plurality of layers to define a step.

17. The surgical instrument according to claim 16, wherein the step includes a first planar surface that extends perpendicularly from the first portion and a second planar surface extending perpendicularly from the first portion along the second portion.

18. The surgical instrument according to claim 16, wherein the conductive layer is disposed between the first portion and the second portion and includes at least one contact disposed on at least one of the first planar surface or the second planar surface of the step.

19. The surgical instrument according to claim 18, wherein the at least one wire is coupled to the at least one contact.

20. The surgical instrument according to claim 19, wherein the at least one contact is coupled to the first planar surface such that the at least one wire extends along the longitudinal axis of the elongated body.

21. The surgical instrument according to claim 19, wherein the at least one contact is coupled to the second planar surface, wherein a first portion of the at least one wire extends perpendicularly from the second planar surface and a second portion of the at least one wire extends perpendicularly from the first portion of the at least one wire and along the longitudinal axis of the elongated body.

* * * * *